United States Patent
Shelton, IV et al.

(10) Patent No.: US 10,675,103 B2
(45) Date of Patent: Jun. 9, 2020

(54) ROBOTICS COMMUNICATION AND CONTROL

(71) Applicant: Ethicon Endo-Surgery, LLC, Guaynabo, PR (US)

(72) Inventors: Frederick E. Shelton, IV, Hillsboro, OH (US); David C. Yates, West Chester, OH (US); Jason L. Harris, Lebanon, OH (US); Kevin L. Houser, Springboro, OH (US); Jeffrey S. Swayze, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 693 days.

(21) Appl. No.: 15/237,946

(22) Filed: Aug. 16, 2016

(65) Prior Publication Data

US 2018/0049823 A1 Feb. 22, 2018

(51) Int. Cl.
| | |
|---|---|
| *A61B 34/30* | (2016.01) |
| *A61B 34/37* | (2016.01) |
| *A61B 34/00* | (2016.01) |
| *A61B 34/35* | (2016.01) |

(52) U.S. Cl.
CPC .............. *A61B 34/30* (2016.02); *A61B 34/37* (2016.02); *A61B 34/74* (2016.02); *A61B 34/35* (2016.02); *A61B 2034/305* (2016.02); *A61B 2034/741* (2016.02); *A61B 2034/742* (2016.02)

(58) Field of Classification Search
CPC .............. A61B 34/30; A61B 2034/741; A61B 2034/305; A61B 2034/742; A61B 34/35; A61B 34/37; A61B 34/74

USPC .................................................. 600/437, 407
See application file for complete search history.

(56) References Cited

U.S. PATENT DOCUMENTS

| | | | | |
|---|---|---|---|---|
| 6,364,888 | B1 * | 4/2002 | Niemeyer | H04N 13/327 606/130 |
| 6,820,349 | B2 * | 11/2004 | Peine | H01L 21/68 33/613 |
| 8,114,345 | B2 | 2/2012 | Dlugos, Jr. et al. | |
| 8,882,792 | B2 | 11/2014 | Dietz et al. | |
| 8,915,842 | B2 | 12/2014 | Weisenburgh, II et al. | |
| 8,931,682 | B2 | 1/2015 | Timm et al. | |
| 8,945,098 | B2 | 2/2015 | Seibold et al. | |
| 10,010,308 | B2 * | 7/2018 | Zhou | A61B 10/04 |

(Continued)

OTHER PUBLICATIONS

Correlated Solutions, "Principle of Digital Image Correlation," 2013 (http://correlatedsolutions.com/digital-image-correlation/).

(Continued)

*Primary Examiner* — Oommen Jacob
(74) *Attorney, Agent, or Firm* — Mintz Levin Cohn Ferris Glovsky and Popeo, P.C.

(57) ABSTRACT

A robotic surgical system having a master controller configured to control a set of basic functions of the components of the robotic surgical system. The components including at least an electromechanical tool, an electromechanical arm, an instrument shaft, and an end effector. At least one secondary controller is disposed within at least one of the components and is configured to control functions of the components in addition to the basic functions controlled by the master controller. The functions of the components controlled by the secondary controller increasing the functionality of the robotic surgical system.

20 Claims, 11 Drawing Sheets

(56) References Cited

U.S. PATENT DOCUMENTS

| | | | |
|---|---|---|---|
| 2003/0010603 A1* | 1/2003 | Corrigan | B65G 29/00 198/474.1 |
| 2003/0097060 A1* | 5/2003 | Yanof | A61B 34/70 600/424 |
| 2003/0108415 A1* | 6/2003 | Hosek | B25J 9/1664 414/783 |
| 2005/0107917 A1* | 5/2005 | Smith | B25J 15/0253 700/245 |
| 2006/0079884 A1* | 4/2006 | Manzo | A61B 18/1442 606/41 |
| 2008/0081948 A1 | 4/2008 | Weisenburgh et al. | |
| 2009/0171244 A1* | 7/2009 | Ning | A61B 6/032 600/567 |
| 2009/0326324 A1* | 12/2009 | Munoz Martinez | A61B 34/30 600/118 |
| 2010/0185087 A1* | 7/2010 | Nields | A61B 18/18 600/439 |
| 2010/0185212 A1* | 7/2010 | Sholev | A61B 34/70 606/130 |
| 2011/0118709 A1 | 5/2011 | Burbank | |
| 2011/0118778 A1* | 5/2011 | Burbank | A61B 17/07207 606/205 |
| 2013/0282052 A1 | 10/2013 | Aranyi et al. | |
| 2013/0317344 A1* | 11/2013 | Borus | A61B 34/76 600/411 |
| 2014/0005718 A1* | 1/2014 | Shelton, IV | A61B 17/07207 606/205 |
| 2015/0073259 A1* | 3/2015 | Zhou | A61B 10/0233 600/411 |
| 2015/0173690 A1* | 6/2015 | Ning | A61B 6/032 600/427 |
| 2015/0223897 A1* | 8/2015 | Kostrzewski | A61B 17/1615 606/130 |
| 2018/0021097 A1* | 1/2018 | Quaid | G06F 19/00 606/130 |
| 2018/0049823 A1* | 2/2018 | Shelton, IV | A61B 34/30 |
| 2018/0243037 A1* | 8/2018 | Bailey | A61B 34/70 |

OTHER PUBLICATIONS

U.S. Appl. No. 15/131,963 entitled "Method for Operating a Surgical Instrument" filed Apr. 18, 2016.

U.S. Appl. No. 15/177,430 entitled "Surgical Instrument With User Adaptable Techniques" filed Jun. 9, 2016.

* cited by examiner

ROBOTICS COMMUNICATION AND CONTROL

FIELD

Methods and devices are provided for robotic surgery, and in particular for distributing communication and control responsibility among the components of robotic surgical systems.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

Minimally invasive robotic systems typically have a base unit that controls the functions of the robotic system. Advances in sensor technology, manufacturing techniques, and the like, have made the provision of additional functionality to surgical tools of these robotic systems. However, the existing base units, which tend to be large and expensive to replace, were not designed for the more advanced or additional functionality.

While significant advances have been made in the field of robotic surgery, there remains a need for improved methods, systems, and devices for use in robotic surgery.

SUMMARY

In one aspect a robotic surgical system is described that facilitates control of functions of the electromechanical components of a robotic system unsupported by a master control system of the robotic surgical system. In one embodiment, the system can include an electromechanical tool configured to perform surgical functions. The electromechanical tool can include an instrument shaft and an end effector formed on the instrument shaft, wherein the end effector is configured to perform a procedure on tissue of a patient. The system can include an electromechanical arm configured for movement in multiple axes. The electromechanical tool can be configured to be mounted on the electromechanical arm, and the electromechanical tool can be configured to move relative to the electromechanical arm.

The system can include a master controller configured to control a set of basic functions of the electromechanical tool. The electromechanical tool may include, at least, the electromechanical arm, the instrument shaft, and the end effector. One or more of the electromechanical tool, the electromechanical arm, the instrument shaft and the end effector are configured to perform a set of additional functions. The additional functions can be unsupported by the robotic surgical system master controller. Secondary controller(s) can be disposed on one or more of the electromechanical tool, the electromechanical arm, the instrument shaft, and the end effector, wherein the secondary controller is configured to control a set of additional functions of the electromechanical tool, the electromechanical arm, the instrument shaft and/or the end effector.

In some embodiments, one or more of the following features may be optionally included in the system. For example, the secondary controller can be configured to control the set of additional functions in response to receiving a request from the master controller. An end effector can include a sensor configured to generate a sensor output and the secondary controller can be configured to control the set of additional functions of the end effector based on the generated output from the sensor. The secondary controller can be in the end effector, tool shaft, puck, tool driver, or the like. The secondary controller can be a single secondary controller or can comprise of multiple secondary controllers performing various sensing and control functions. For example, the end effector may include a secondary controller for controlling additional functions of the end effector, and the instrument shaft can include a status processor configured to monitor the status of the end effector.

The system can include a puck that includes a puck controller configured to receive input from one or more sensors disposed on the instrument shaft and/or the end effector, and configured to control the movement of the instrument shaft and/or the end effector based on the input received from the one or more sensors disposed on the instrument shaft and/or end effector. The puck controller can be configured to generate an output for transmission to the master controller. The output generated by the puck controller can include a status of the puck, instrument shaft, the end effector, and/or other components of the system. Examples of control can include the puck controller being configured to control a rotation angle of the instrument shaft, control a rotation of the distal head of the end effector, or the like.

In some embodiments, the instrument shaft can include a first articulation joint controlled by an input received from the master controller, a second articulation joint, and an instrument shaft controller configured to control the movement of the second articulation joint. The instrument shaft controller can be configured to transmit a status of the second articulation joint to the master controller. The puck can be configured to control one or more of the functions of the instrument shaft, the end effector and/or other component of the system. The instrument shaft controller can be configured to transmit a status of the second end articulation joint to the puck.

The system can include a user interface that includes a user control having a plurality of modes. One mode of the plurality modes can be configured to facilitate activation of the set of additional functions of the electromechanical tool, the electromechanical arm, the instrument shaft and/or the end effector.

The master controller can be configured to provide power to one or more of the electromechanical tool, the electromechanical arm, the instrument shaft and the end effector. Power supplies can be provided for the electromechanical tool, the electromechanical arm, the instrument shaft, the end effector and/or other components for supporting additional functionality of the electromechanical tool, the electromechanical arm, the instrument shaft, the end effector and/or other components.

BRIEF DESCRIPTION OF THE DRAWINGS

The invention will be more fully understood from the following detailed description taken in conjunction with the accompanying drawings, in which.

DETAILED DESCRIPTION

Figure 1:
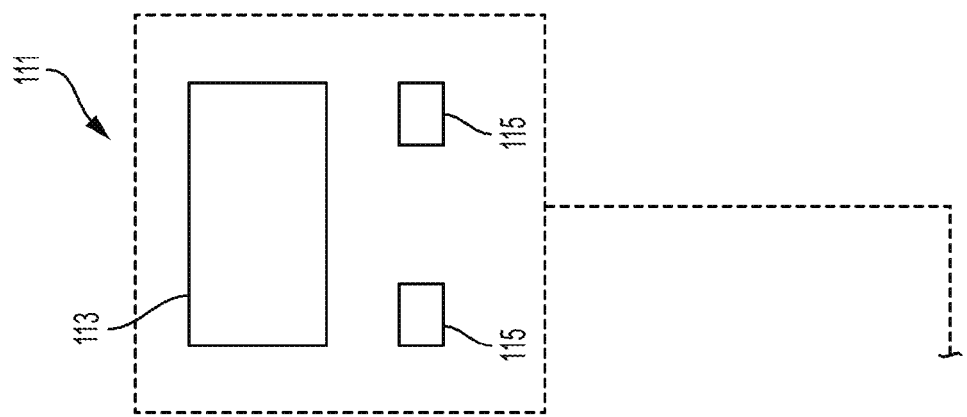
FIG. 1 is a perspective view of an embodiment of a surgical robotic system.
Figure 1:
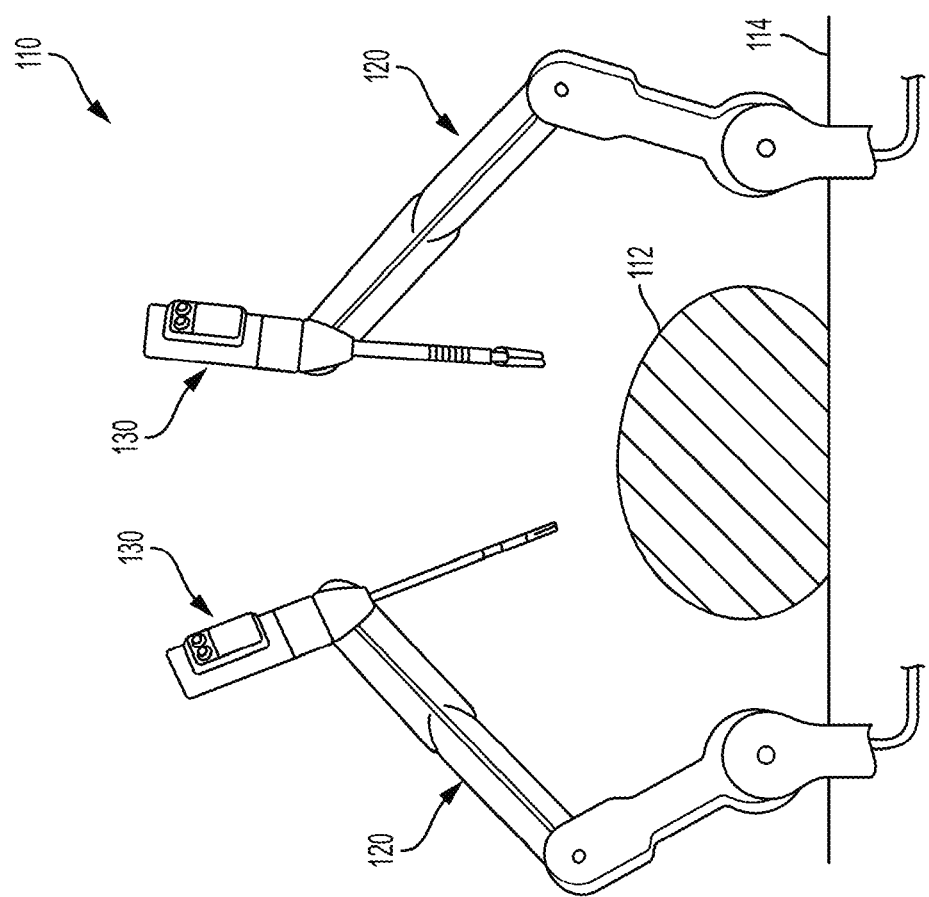

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, robotic surgical systems typically have a plurality of electromechanical components disposed between, and including, a central master control unit having a master controller and an end effector configured to perform surgical functions on the tissue of a patient. The plurality of electromechanical components can each have one or more degrees of freedom which can be facilitated by one or more actuators in each electromechanical component. The actuators in each of the electromechanical components are typically controlled by a master controller.

Processing and control of the electromechanical components require the master controller to be programmed to control the actuators. Once a master control unit is installed, for example in a hospital operating room, it typically cannot be reprogrammed to be able to control new electromechanical components that are developed.

The presently described subject matter relates to the hierarchy of the control of electromechanical components of a robotic surgical system. That is, the electromechanical components of the robotic surgical system can have functionality in addition to the functionality supported by the master controller. One or more electromechanical components can be provided that have processing and control capabilities to support the additional functionality of the electromechanical components. In some variations, an electromechanical component having additional functionality can be controlled by processors and controllers disposed on or in the electromechanical component, or it can be controlled by processors and controllers disposed on an upstream electromechanical component.

Without limiting the scope of this disclosure, a functional benefit of the presently described subject matter includes providing additional functionality and capabilities to a robotic surgical system that was not originally capable of performing those additional functions and capabilities.

Robotic Surgical Systems

The systems, devices, and methods disclosed herein can be implemented using a robotic surgical system.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 100 that includes a patient-side portion 110 that is positioned adjacent to a patient 112, and a user-side portion 111 that is located a distance from the patient, either in the same room and/or in a remote location. The patient-side portion 110 generally includes one or more electrical mechanical components. The one or more electrical mechanical components can include one or more robotic arms 120 and one or more tool assemblies 130 that are configured to releasably couple to a robotic arm 120. The user-side portion 111 generally includes a vision system 113 for viewing the patient 312 and/or surgical site, and a master control system 115 for controlling the movement of the robotic arms 120 and each tool assembly 130 during a surgical procedure. The vision system 113 can be connected to one or more visual sensors, for example, cameras, for viewing the patient 112.

The master control system 115 can have a variety of configurations and it can be located adjacent to the patient, e.g., in the operating room, remote from the patient, e.g., in a separate control room, remote from the operating room, or it can be distributed at two or more locations. For example, a dedicated system control console can be located in the operating room, and a separate console can be located in a remote location. The master control system 115 can include components that enable a user to view a surgical site of a patient 112 being operated on by the patient-side portion 110 and/or to control one or more parts of the patient-side portion 110 (e.g., to perform a surgical procedure at the surgical site 112). In some embodiments, the master control system 115 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 120 and tool assemblies 130.

Figure 3:
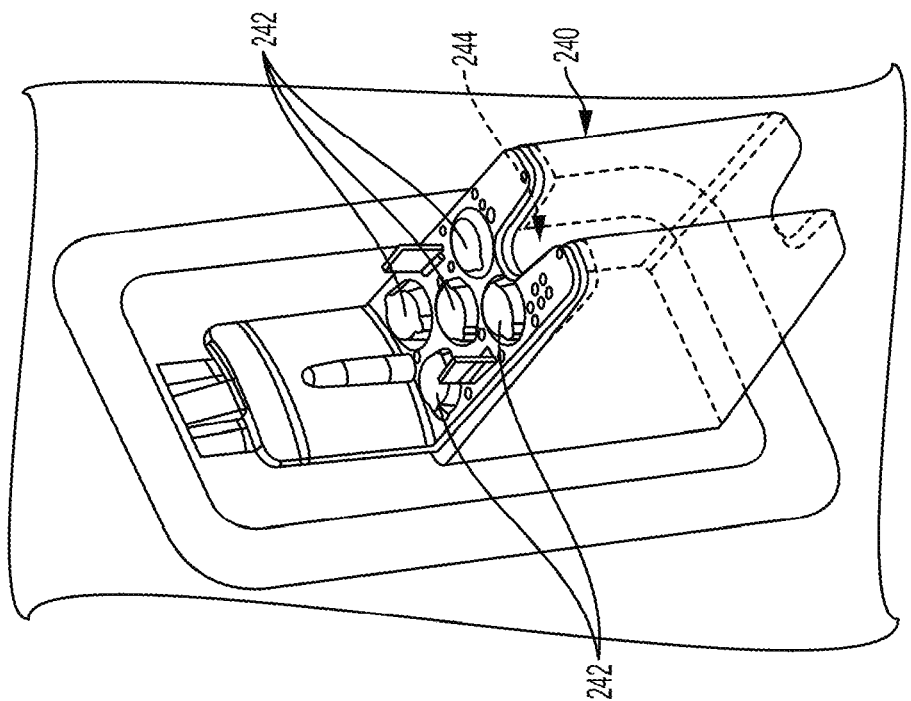
FIG. 3 illustrates the tool driver of FIG. 2 in more detail.

The patient-side portion can also have a variety of configurations. As depicted in FIG. 3, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 3). Alternatively, the patient-side portion 310 can include a single assembly that includes one or more robotic arms 320 extending therefrom.

Figure 2:
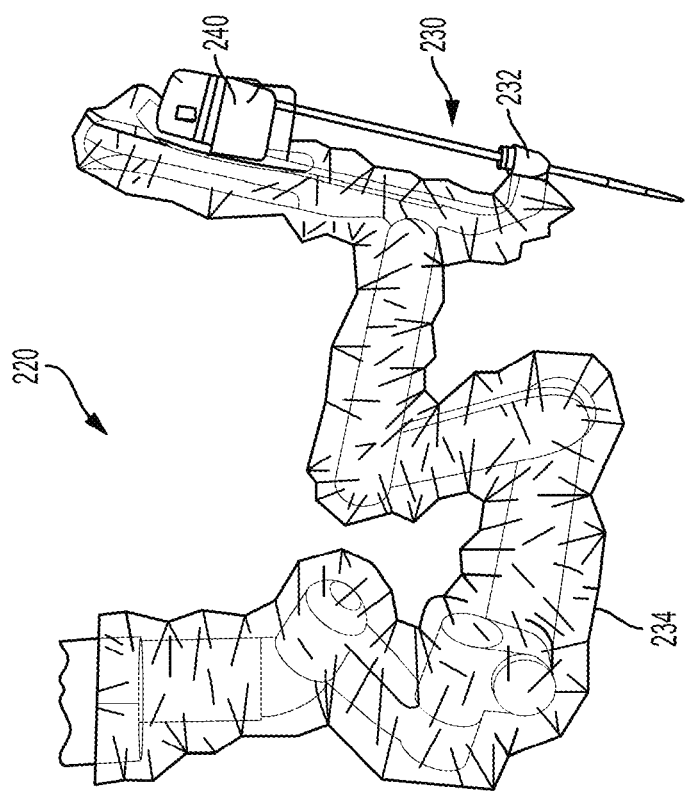
FIG. 2 illustrates an embodiment of a robotic arm and a tool assembly releasably coupled to the robotic arm.
Figure 9:
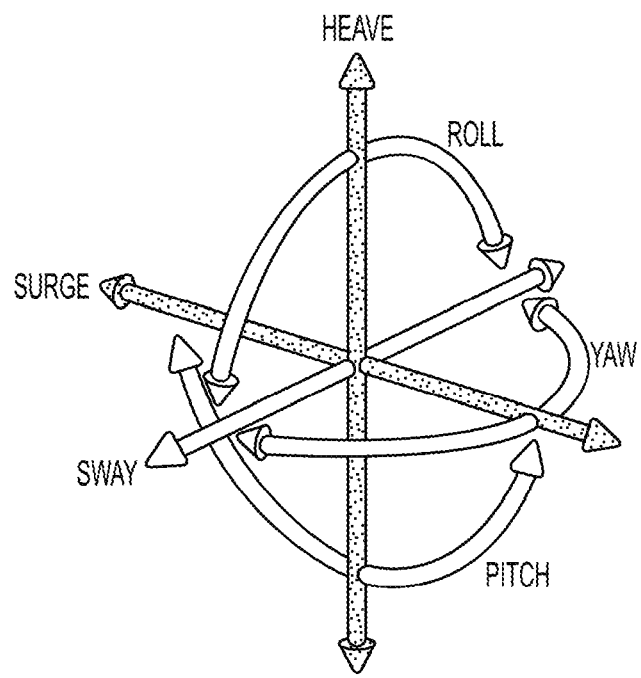
FIG. 9 illustrates movement and rotation along one of the three axes in a Cartesian frame.

FIG. 2 illustrates an embodiment of a robotic arm 220 and a tool assembly 230 releasably coupled to the robotic arm 220. The robotic arm 220 can support and move the associated tool assembly 230 along one or more mechanical degrees of freedom (e.g., all six Cartesian degrees of freedom, as illustrated in FIG. 9, five or fewer Cartesian degrees of freedom, etc.).

The robotic arm 220 can include a tool driver 240 at a distal end of the robotic arm 220, which can assist with controlling features associated with the tool assembly 230. The robotic arm 220 can also include an entry guide 232 (e.g., a cannula mount or cannula) that can be a part of or removably coupled to the robotic arm 220, as shown in FIG. 3. A shaft 236 of the tool assembly 230 can be inserted through the entry guide 230 for insertion into a patient.

In order to provide a sterile operation area while using the surgical system, a barrier 234 can be placed between the actuating portion of the surgical system (e.g., the robotic arm 220) and the surgical instruments (e.g., the tool assembly 230). A sterile component, such as an instrument sterile adapter (ISA), can also be placed at the connecting interface between the tool assembly 230 and the robotic arm 220. The placement of an ISA between the tool assembly 230 and the robotic arm 220 can ensure a sterile coupling point for the tool assembly 230 and the robotic arm 220. This permits removal of tool assemblies 230 from the robotic arm 220 to exchange with other tool assemblies 230 during the course of a surgery without compromising the sterile surgical field.

FIG. 3 illustrates the tool driver 240 in more detail. As shown, the tool driver 440 includes one or more motors, e.g., five motors 242 are shown, that control a variety of movements and actions associated with the tool assembly 230, as will be described in greater detail below. For example, each motor 242 can couple to and/or interact with an activation feature (e.g., gear) associated with the tool assembly 230 for controlling one or more actions and movements that can be performed by the tool assembly 230, such as for assisting with performing a surgical operation. The motors 242 are accessible on the upper surface of the tool driver 240, and thus the tool assembly is configured to mount on top of the tool driver 240 to couple thereto. The tool driver 240 also includes a shaft-receiving channel 244 formed in a sidewall thereof for receiving the shaft of the tool assembly 230. In other embodiments, the shaft can extend through on opening in the tool driver 240, or the two components can mate in various other configurations.

Figure 4:
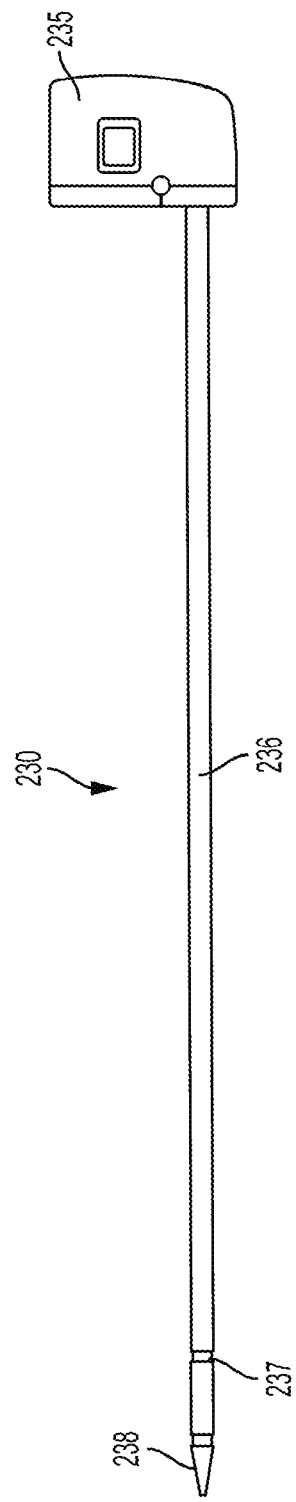
FIG. 4 illustrates the tool assembly uncoupled from the robotic arm.

FIG. 4 illustrates the tool assembly 230 uncoupled from the robotic arm 220. The tool assembly 230 includes a housing or puck 235 coupled to a proximal end of a shaft 236 and an end effector 238 coupled to a distal end of the shaft 236. The puck 235 can include coupling features that assist with releasably coupling the puck 235 to the tool driver 240 of the robotic arm 220. The puck 235 can include gears and/or actuators that can be actuated by the one or more motors 242 in the driver 240, as will be described in greater detail below. The gears and/or actuators in the puck 235 can control the operation of various features associated with the end effector 238 (e.g., clamping, firing, rotation, articulation, energy delivery, etc.), as well as control the movement of the shaft 236 (e.g., rotation of the shaft).

The shaft 236 can be fixed to the puck 235, or it can be releasably coupled to the puck 235 such that the shaft 236 can be interchangeable with other shafts. This can allow a single puck 235 to be adaptable to various shafts 236 having different end effectors 238. The shaft 236 can include actuators and connectors that extend along the shaft and assist with controlling the actuation and/or movement of the end effector 238 and/or shaft 236. The shaft 236 can also include one or more joints or wrists 237 that allow a part of the shaft 236 or the end effector 438 to articulate relative to the longitudinal axis of the shaft 236. This can allow for fine movements and various angulation of the end effector 238 relative to the longitudinal axis of the shaft 236. The end effector 238 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
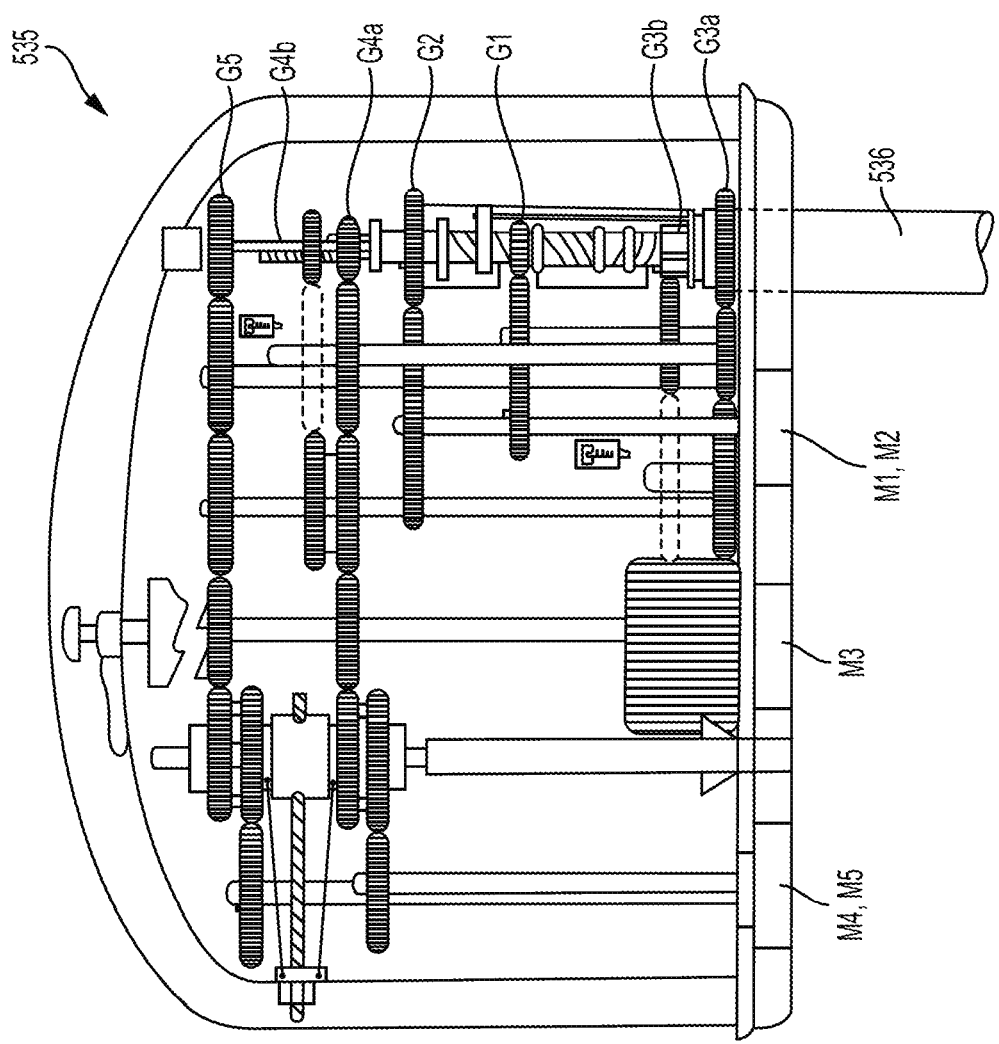
FIG. 5 illustrates an embodiment of a puck and a proximal end of a shaft extending from the puck.

FIG. 5 illustrates an embodiment of a puck 535 and a proximal end of a shaft 536 extending from the puck 535. As shown in FIG. 5, the puck 535 includes a plurality of actuation gears and gear shafts that can be either directly or indirectly controlled by any one of the motors 242 associated with the driver 240. For example, as shown in FIG. 5, the puck 535 is configured to couple to five motors at the locations indicated by reference numbers M1, M2, M3, M4, and M5. In this embodiment, puck 535 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 238 in desired left and right directions. The puck 535 also includes a shaft rotation gear G3a that is coupled to the third motor M3 via a series of one or more additional gears and shafts. Actuation of the third motor M3 will thus rotate the shaft rotation gear G3a thereby causing rotation of the shaft 236 of the tool assembly 230. The third motor M3 can also be configured to shift and to couple, via a series of one or more additional gears and shafts, to a head rotation gear G3b, which will cause rotation of the end effector 238 relative to the shaft 236. The puck 535 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector 238. The puck 535 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector 238. Finally, the illustrated puck 535 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 238, as will be discussed in more detail below.

Figure 6:
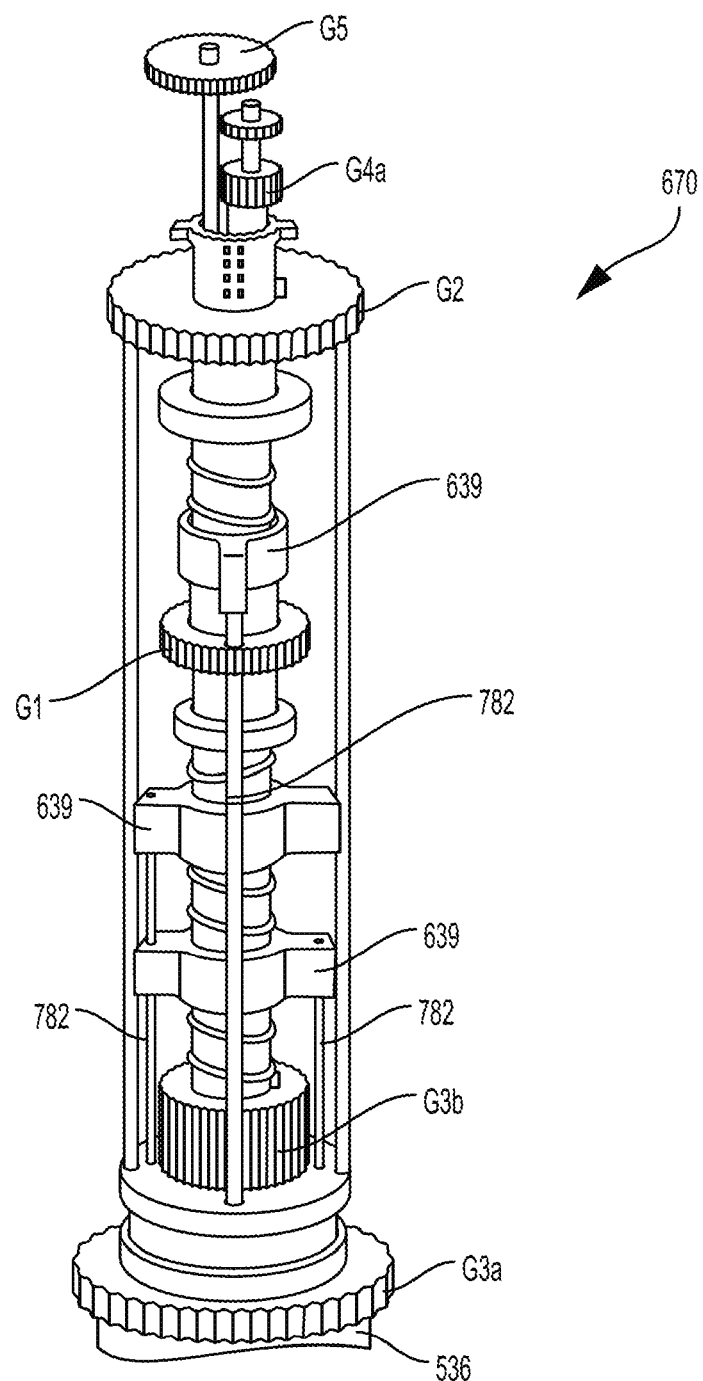
FIG. 6 illustrates the actuation assembly components of the puck of FIG. 5.
Figure 7:
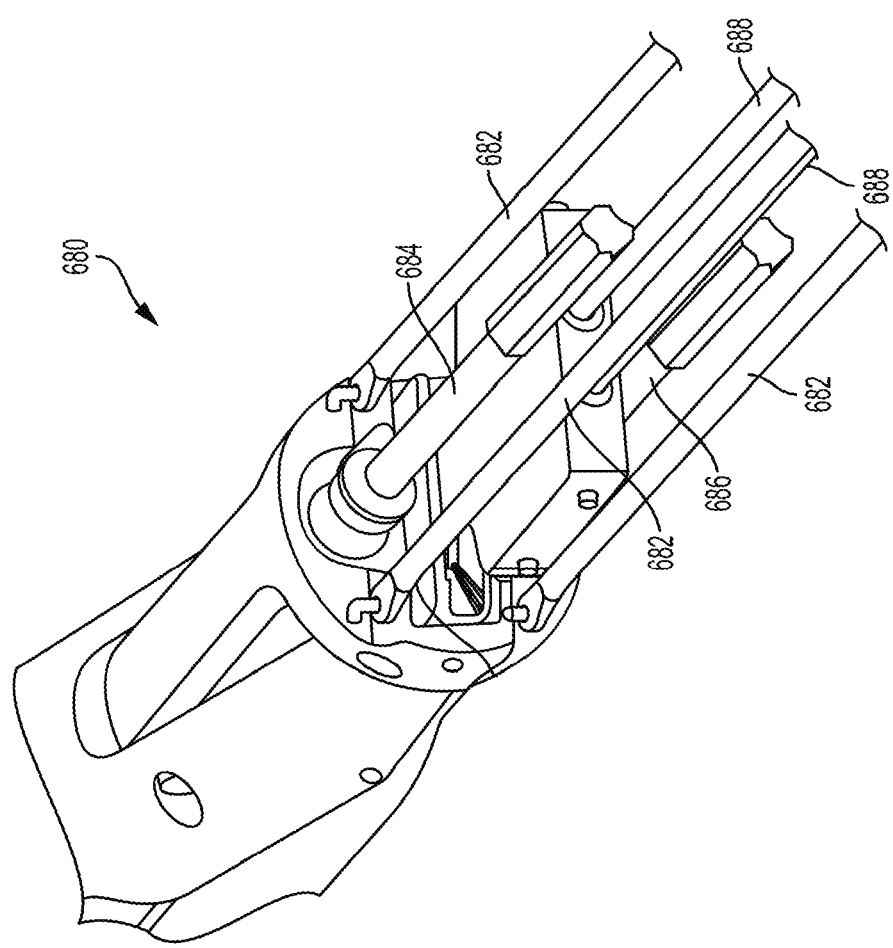
FIG. 7 illustrates a distal end of the actuation shafts extending from a wrist located just proximal of the end effector.

FIG. 6 illustrates the actuation assembly 670 components of the puck of FIG. 5. As shown and indicated above, each of the gears G1-G5 is coupled to an actuation shaft that extends from the actuation assembly 670 and along the shaft 236 of the tool assembly 230, such as for controlling the movements of the end effector. FIG. 7 illustrates a distal end of the actuation shafts extending from a wrist 780 located just proximal of the end effector 238. The wrist 780 can allow for fine movements and angulation of the end effector 438 relative to the proximal end of the shaft 236. As shown in FIG. 7, the wrist 780 includes four articulation cables 782 that are spaced around a perimeter of the wrist 780. When actuated (e.g., pushed, pulled, rotated), the articulation cables 782 will cause articulation of the end effector 238 (e.g., movement up, down, left, right, and combinations thereof) relative to the proximal end of the shaft 236. The articulation cables 782 are connected to the articulation couplers 639, shown in FIG. 6, that are driven proximally and distally when the articulation gears G1, G2 are actuated by the first and second motors M1, M2. The wrist 780 also includes an upper rotary driver 784 that when actuated can cause the pair of jaws of the end effector 238 to firmly close. The upper rotary driver 784 is coupled to the firm close gear G4a shown in FIG. 6 such that rotation of the firm close gear G4a by the motor M4 causes rotation of the rotary driver 784. The wrist 780 can also include a lower rotary driver 786 that when actuated can cause movement of a sled located at the end effector 238. The lower rotary driver 786 is coupled to the firing gear G5 shown in FIG. 6 and it likewise rotates in response to rotation of the firing gear G5. The illustrated wrist 780 further includes a linear pull cable 788 that is coupled to the quick close gear G4b shown in FIG. 6 and that moves linearly in a proximal direction to cause rapid close of the pair of jaws.

Figure 8:
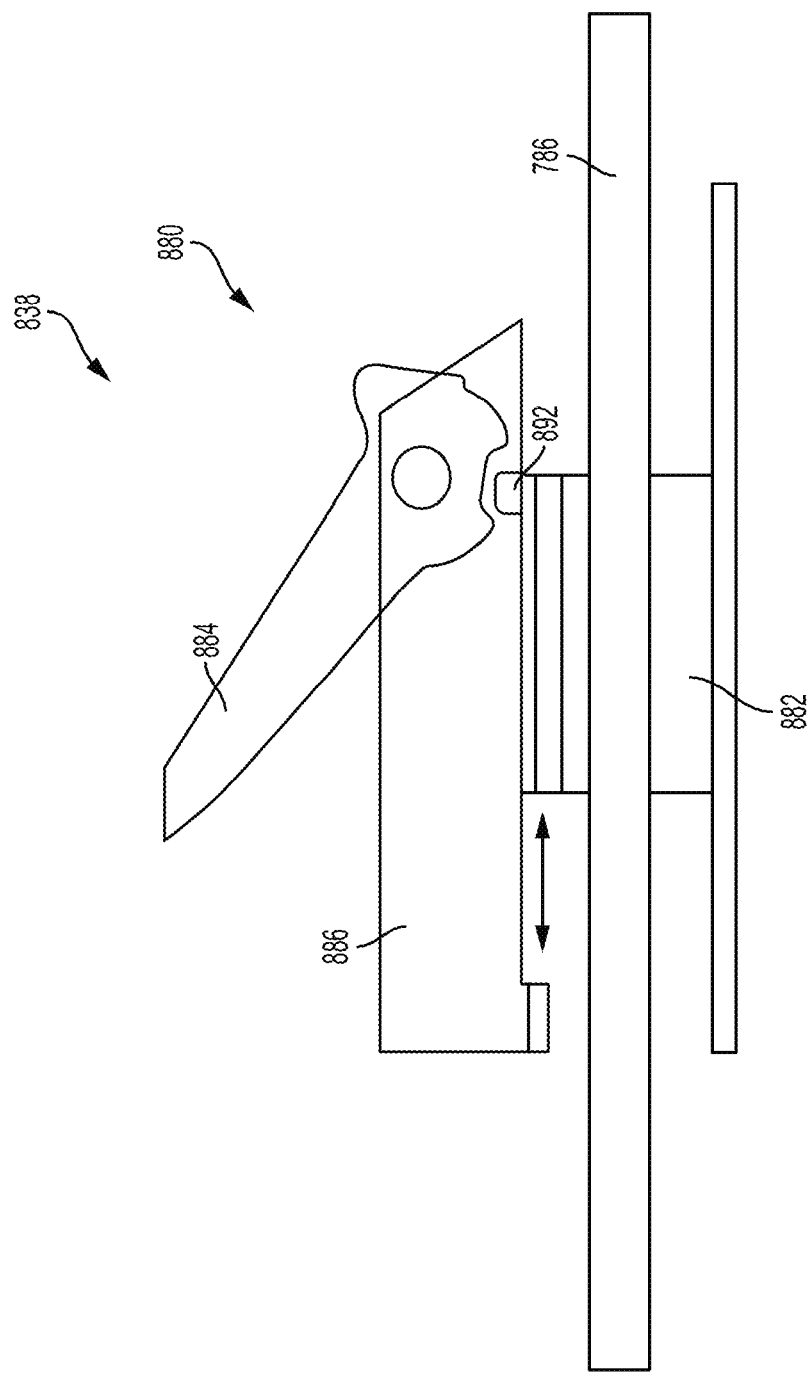
FIG. 8 illustrates a portion of an end effector having a knife actuation assembly.

FIG. 8 illustrates a portion of an end effector 838 having a knife actuation assembly 880 that includes a drive member 882, a knife 884, a knife sled 886, and a lead screw or rotary driver 786. The drive member 882 includes internal threads that are threadably coupled with the rotary driver 786. Such coupling can allow drive member 882 to move along the rotary driver 986 when the rotary driver 786 is rotated. As discussed above, the rotary driver 786 can be actuated at the wrist 780, as shown in FIG. 7, thereby causing rotation of the rotary driver 786 and linear movement of the knife sled 886 along the rotary driver 786. The rotary driver 786 is coupled to the firing gear G5 shown in FIG. 6. The knife actuation assembly 880 is configured to orient the knife 884 in a cutting position when the drive member 882 pushes the knife sled 886 along the rotary driver 786 and to stow the knife 884 when the drive member 882 is moved proximally relative to the knife sled 886. In operation, the rotary driver 786 is first rotated to advance the drive member 882 distally along the rotary driver 786 thereby pushing the knife sled 886 in the distal direction and angularly orienting the knife 884 in the cutting position. At the end of the distal movement of the assembly 880, the direction of rotation of the rotary driver 786 is reversed to retract the drive member 882 proximally relative to the knife sled 886, thereby causing the knife 884 to rotate down into the stowed position, such as via interaction between an interface feature 892 and the knife 884.

Terminology

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 9, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in analog circuitry, digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 10:
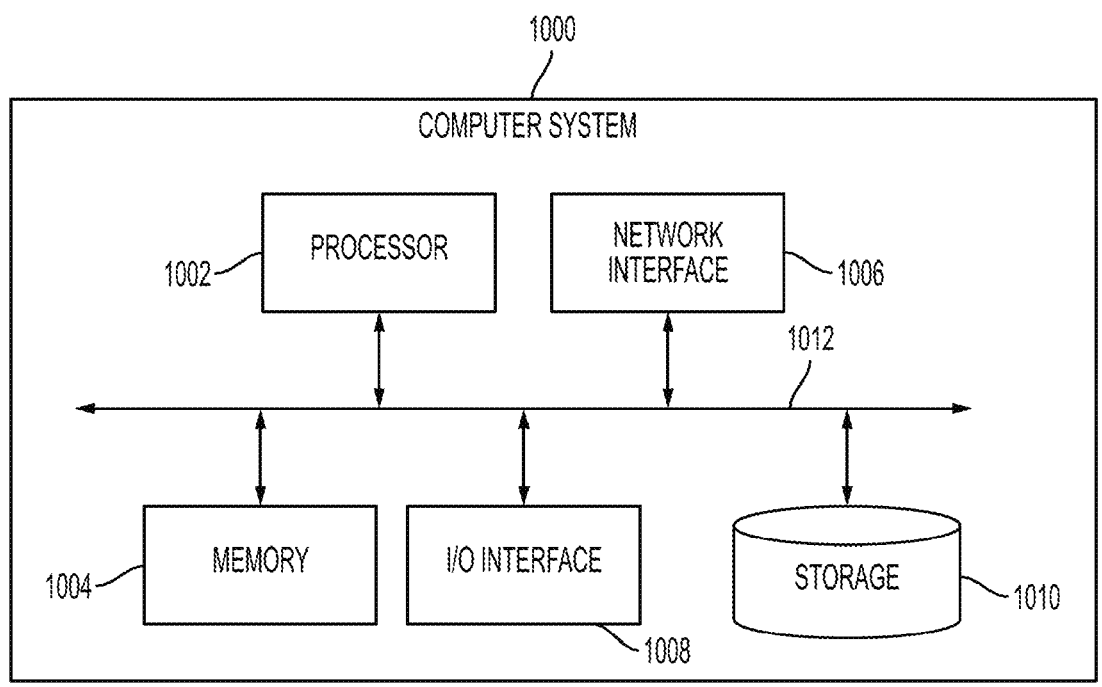
FIG. 10 illustrates one exemplary embodiment of a computer system having one or more features consistent with the present description.

FIG. 10 illustrates one exemplary embodiment of a computer system 1000. As shown, the computer system 1000 includes one or more processors 1002 which can control the operation of the computer system 1000. "Processors" are also referred to herein as "controllers." The processor(s) 1002 can include any type of microprocessor or central processing unit (CPU), including programmable general-purpose or special-purpose microprocessors and/or any one of a variety of proprietary or commercially available single or multi-processor systems. The computer system 1000 can also include one or more memories 1004, which can provide temporary storage for code to be executed by the processor(s) 1002 or for data acquired from one or more users, storage devices, and/or databases. The memory 1004 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1000 can be coupled to a bus system 1012. The illustrated bus system 1012 is an abstraction that represents any one or more separate physical busses, communication lines/interfaces, and/or multi-drop or point-to-point connections, connected by appropriate bridges, adapters, and/or controllers. The computer system 1000 can also include one or more network interface(s) 1006, one or more input/output (IO) interface(s) 1008, and one or more storage device(s) 1010.

The network interface(s) 1006 can enable the computer system 1000 to communicate with remote devices, e.g., other computer systems, over a network, and can be, for non-limiting example, remote desktop connection interfaces, Ethernet adapters, and/or other local area network (LAN) adapters. The IO interface(s) 1008 can include one or more interface components to connect the computer system 100 with other electronic equipment. For non-limiting example, the IO interface(s) 1008 can include high speed data ports, such as universal serial bus (USB) ports, 1394 ports, Wi-Fi, Bluetooth, etc. Additionally, the computer system 1000 can be accessible to a human user, and thus the IO interface(s) 108 can include displays, speakers, keyboards, pointing devices, and/or various other video, audio, or alphanumeric interfaces. The storage device(s) 1010 can include any conventional medium for storing data in a non-volatile and/or non-transient manner. The storage device(s) 1010 can thus hold data and/or instructions in a persistent state, i.e., the value(s) are retained despite interruption of power to the computer system 1000. The storage device(s) 1010 can include one or more hard disk drives, flash drives, USB drives, optical drives, various media cards, diskettes, compact discs, and/or any combination thereof and can be directly connected to the computer system 1000 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 10 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 1000 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 1000 can also include a web server for generating and/or delivering the web pages to client computer systems.

In an exemplary embodiment, the computer system 1000 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

Figure 11:
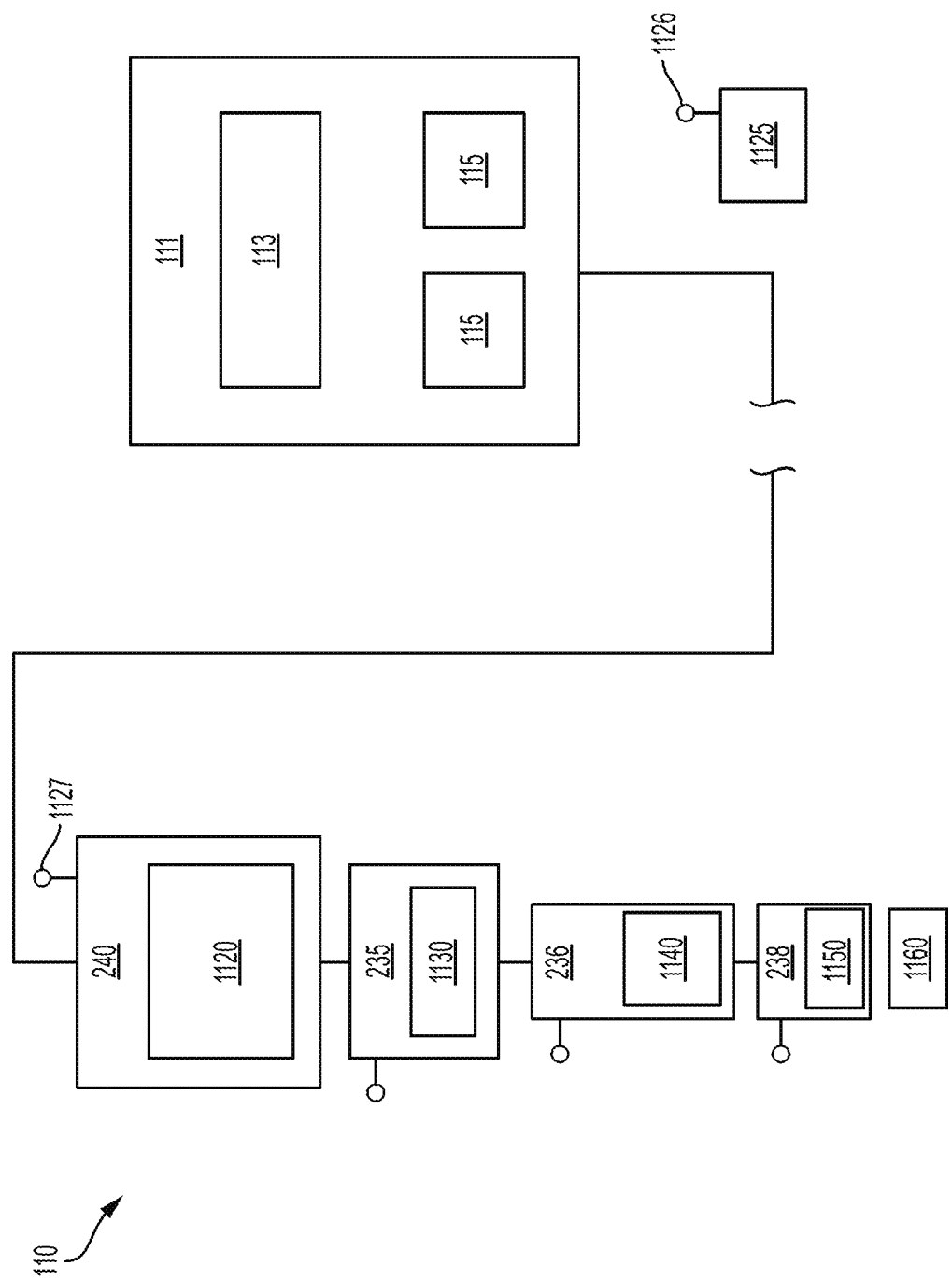
FIG. 11 is a block diagram of the secondary controllers of a robotic surgical system having one or more features consistent with the presently described subject matter.
Figure 12:
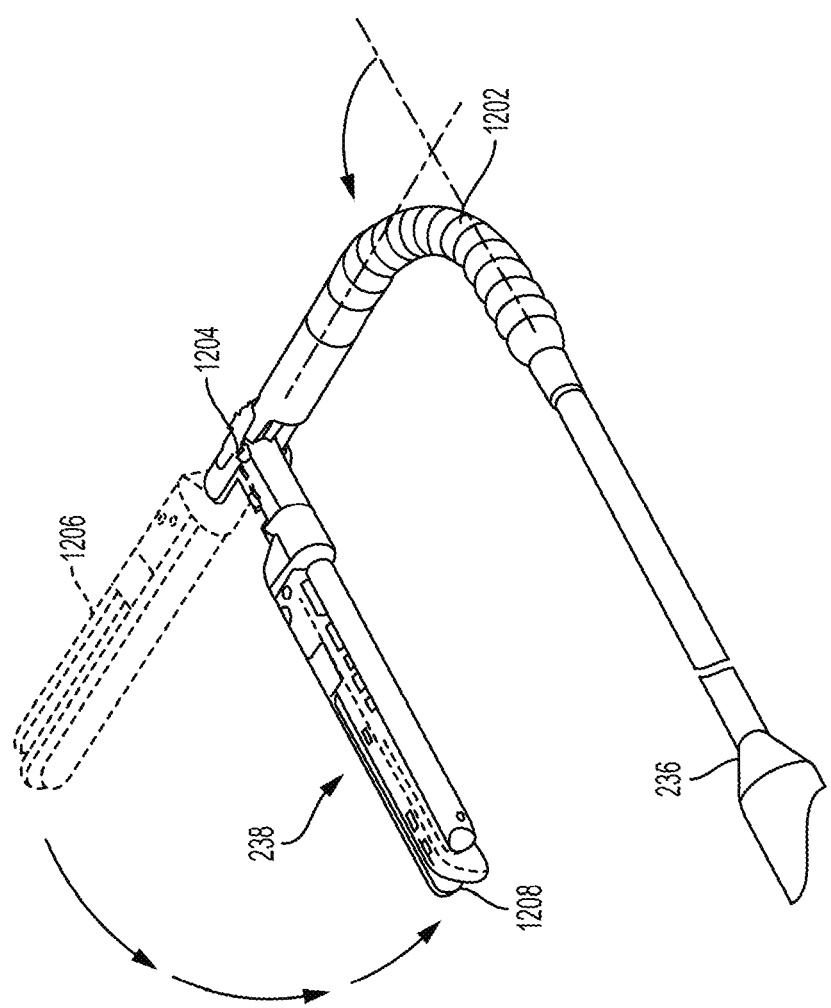
FIG. 12 is an illustration of an end effector attached to a shaft of a tool assembly that is coupled to a robotic arm.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Additional Functionality Reference is now made to FIGS. 11 and 12. FIG. 11 is a block diagram of the secondary controllers of a robotic surgical system having one or more features consistent with the presently described subject matter. FIG. 12 is an illustration of an end effector 238 attached to a shaft 236 of a tool assembly that is coupled to a robotic arm. FIG. 11 illustrates user side system 111 having vision system 113 and main controllers 115. An auxiliary control system 1125 can also be present. The patient side system 110 includes tool driver 240 having a tool driver secondary controller 1120, puck 235 having puck secondary controller 1130, shaft 236 having shaft secondary controller 1140, and end effector 238 having end effector secondary controller 1150. The patient side 110 is also shown to have a sensor 1160. Although each of the puck, the shaft, the tool driver, and the end effector is shown to have its own secondary control system, it is understood that each of these components need not each have its own secondary controller and that some of the components can have more than one secondary controller. The secondary controller associated with each of the components such as the puck, the shaft, the tool driver, and the end effector can allow the associated component (or downstream components) to perform functions in addition to the functions that the master control system 115 is configured to control. For example, as shown in FIG. 11, includes shaft controller 1140, which can be configured to perform processing and control of additional functions of the shaft 236 and/or end effector 238.

The end effector 238 shown in FIG. 12 has a first articulation joint 1202, which can be an originally designed articulation joint. The master control system 115 can be configured to control the first articulation joint 1202 directly or indirectly through a secondary controller, such as the tool driver secondary controller 1120, the puck secondary controller 1130, shaft secondary controller 1140, end effector secondary controller 150, or the like. The end effector 238 of FIG. 12 also includes a second articulation joint 1204. The second articulation joint 1204 may be an articulation joint that the master control system 115 is not configured to control. The function of the second articulation joint 1204 can be processed and controlled by one or more secondary controllers, such as end effector secondary controller 1150, shaft secondary controller 1140, puck secondary controller 1130, tool drive secondary controller 1120, or the like.

The second articulation joint 1204 can be configured to facilitate movement of the end of the effector 238 in a direction previously unsupported by the robotic control system. For example, the second articulation joint 1204 can be configured to move the end effector from a first position 1206, which was previously the maximum range of movement in a particular direction, to a second position 1208 which is an extension to the original range of motion.

Similarly, the puck 235 can include a puck secondary controller 1130. The puck secondary controller 1130. The puck secondary controller 1130 can be configured to control at least a portion of the functionality of the puck 235 and to control at least a portion of the functionality of the one or more downstream electromechanical components of the robotic surgical system. Downstream electromechanical components can include, for example, the shaft 236, end effector 238, or the like.

The end effector 238 may include an end effector secondary controller 1150. The end effector secondary controller 1150 can be configured to process and control one or more features of the end effector 238 and/or provide information about the state of the end effector 238 to upstream components. The end effector secondary controller 1150 can be configured to communicate with, and provide information about the state of the end effector 238 to, the master control system 115. In some embodiments, the end effector secondary controller 1150 can be configured to communicate with one or more other secondary controllers, such as the shaft secondary controller 1140, puck secondary controller 1130, tool driver secondary controller 1120, or the like. Communication between one or more of the secondary controllers can occur without involving the master control system 115.

One or more sensors, such as sensor 1160, can be embedded in the various components of a robotic surgical system. The one or more sensors can be configured to detect a state of the various components of the robotic surgical system and/or the state of an environment in proximity to the one or more sensors. A state of a component can include the degree of articulation and/or angle of rotation of a joint, a temperature of a component, a power level of a battery disposed within a component, a health of a component, or the like. A state of an environment in proximity to the component can include a temperature and/or other property (such as impedance) of the tissue of a patient, the humidity of the atmosphere around the patient, or the like.

Figure 13:
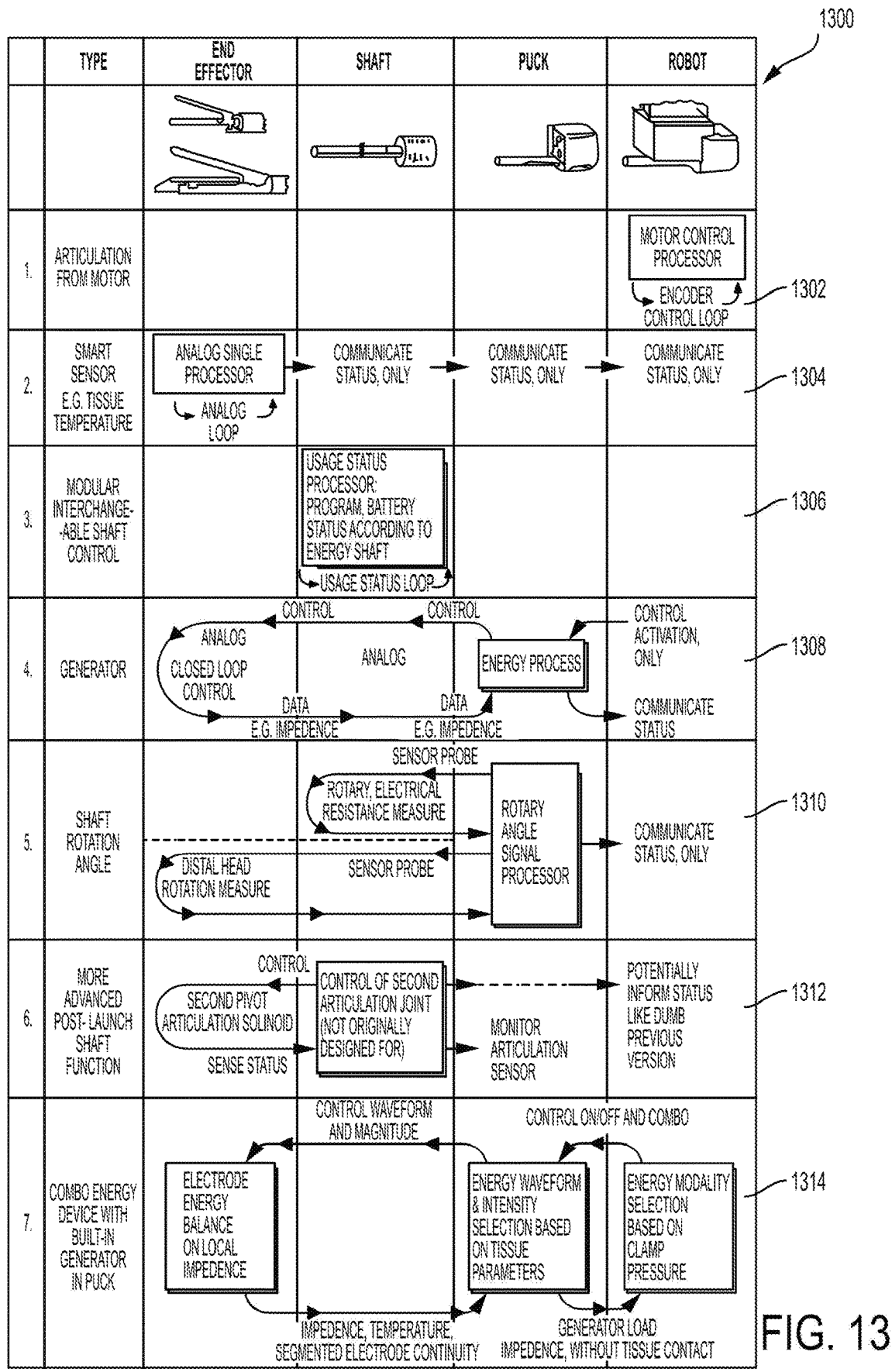
FIG. 13 is a table showing the interaction of the components of a robotic surgical system having one or more features consistent with the present description.

FIG. 13 is a table 1300 showing the interaction of the components of a robotic surgical system having one or more features consistent with the present description. At 1302, the master control system 115, as illustrated in FIG. 1, can be configured to control one or more components of the robotic surgical system. The master control system 115 can be configured to send control signals to the tool driver 240, the puck 235, the shaft 236, and the end effector 238, as described with respect to FIGS. 1-4. The processing and control capabilities provided by the master control system 115 can include a set of basic processes and controls for the components of the robotic surgical system. The basic processes can include, for example, functions such as grasping, cutting, retracting, suturing and the like.

At 1304, a state of an environment in the vicinity of one or more of the components can be detected by a sensor. In the illustrated exemplary embodiment, the state of the environment is a tissue temperature of the patient. The sensor, such as sensor 1160 illustrated in FIG. 11, can be disposed within a component of the robotic surgical system, or it can be positioned remote from the components of the robotic surgical system. As depicted in FIG. 13, the end effector has a signal processor disposed therein, which can facilitate monitoring of the temperature of the patient. The output of the signal processor, e.g., the temperature of the tissue of the patient and/or a determination that the temperature is above or below a threshold value, can be transmitted from the end effector upstream to the master control system 115. The master control system 115 can be configured to display the information obtained from the sensor 1160 on a visual display of a computing system. While the sensor 1160 is illustrated as being at the end of the end effector 238 in FIG. 11, the sensor 1160 can be disposed anywhere on the shaft, the robotic system, in the operating room, or the like.

At 1306, a modular interchangeable shaft control can be facilitated. A shaft of the robotic surgical system, such as shaft 236, can comprise a secondary controller 1140 configured to monitor the usage state of the shaft. For example, the shaft 236 may include a battery providing power to one or more components of the shaft 236 and/or the end effector 238. The one or more components of the shaft 236 and/or the end effector 238 can be configured to perform additional functionality that requires power in addition to the power provided by the master control system 115. The secondary controller 1140 disposed in the shaft 236 can be configured to monitor the charge level, health, etc., of the battery. The master control system 115 may not have been designed to receive information associated with the health of components within the shaft 236 or the end effector 238. Consequently, the information about the status of the health of the components of the shaft 236 and/or end effector 238 may be provided to a remote monitoring unit, indicated on the shaft through visual displays on the surface of the shaft, or the like.

At 1308, a two-way communication process is shown between the various components of the robotic surgical system. In the scenario shown in at 1308, the master control system, such as master control system 115, can provide an activation instruction to a puck 235 or tool driver 240 to activate a functionality of the puck 235 or tool driver 240. The puck 235 or tool driver 240 can have a secondary controller, such as puck secondary controller 1120 or tool driver secondary controller 1130 illustrated in FIG. 11, that can receive the activation instruction and process and control one or more functions of the puck 235 or tool driver 240.

Upon activation of one or more of the functions controlled by the controller disposed within the puck 235 or tool driver 240, information about the state of the end effector 238 and/or the state of an environment in the vicinity of the end effector 238 is communicated to master control system 115. Examples of information about the state of the end effector can include an indication of the angle of articulating joint(s) of the end effector, a temperature of a distal tip of the end effector, a temperature of the tissue in the vicinity of the distal tip of the end effector, an impedance between two jaws at the distal tip of the end effector, or the like. The impedance between two jaws at the distal tip of the end effector can provide an indication of an amount of tissue between the two jaws or the state of tissue treatment of the tissue between the two jaws, etc.

The puck secondary controller 1130 or tool driver secondary controller 1120 can be configured to process the information from the end effector 238 and control the actions of the end effector based on the outcome of the processing of the information from the end effector. The puck secondary controller 1130 or tool driver secondary controller 1120 can be configured to provide a status of the end effector 238 to the master control system 115. Apart from providing the initial activation instruction for a particular function, the master control system 115 may be configured to have no other involvement in the processing and control of that function of the end effector 238. The necessary processing and control of the electromechanical components of the robotic surgical system for performing the function can be carried out by secondary controllers downstream of the master control system 115.

In one exemplary embodiment, puck 235 and/or tool driver 240 can include an ultrasound transducer as a means of communication of data via acoustic or conducted vibrations. The ultrasound transducer can be configured to convert ultrasound waves into electrical signals, or vice versa. Signals generated by the ultrasound transducer can be received at secondary controllers upstream from the ultrasound transducer. The secondary controllers upstream from the ultrasound transducer can be configured to process the signals and cause the electromechanical components of the robotic surgical system to react in response to the processing of the signals generated by the ultrasound transducer. The data communication can be at virtually any frequency that is conducive for use with the transducers and the surgical environment. Similarly, optical communication channels can be employed to achieve communication between various controllers.

At 1310, a process is illustrated for monitoring and controlling a rotation angle of the shaft 236 and/or end effector 238. The status of the rotation angle can be provided to the master control system 115 from one or more secondary controllers downstream of the master control system 115. The tool driver 240, puck 235, and/or shaft 236 can have one or more secondary controllers configured to process and control the functions of the tool driver, puck, or shaft to achieve the desired rotation angle. There can be multiple components of rotation between the distal tip of the end effector and the tool driver. The secondary controller at the tool driver 240 and/or puck 235 can be configured sense a rotation amount of the distal head of the end effector 238. The secondary controller 1120 at the tool driver 240 and/or the secondary controller 1130 puck 235 can be configured to sense a rotation of the shaft 236. For example, the secondary controller 1120 at the tool driver 240 and/or the secondary controller 1130 at the puck 235 can be configured to cause a current that passes through the shaft 236 and back to the secondary controller 1120 at the tool driver 240 and/or the secondary controller 1130 at the puck 235. The amount of resistance on the electrical current can depend on the amount of rotation of the shaft 236 relative to an initial position. The level of resistance can be measured by a secondary controller allowing the secondary controller to determine the angle of rotation of the shaft 236. The secondary controller can communicate the status of the shaft and/or end effector upstream to the master control system 115.

At 1312, one or more secondary controllers can be configured to process and control additional functionality of one or more electromechanical components of the robotic surgical system. The additional functionality of the one or more electromechanical components of the robotic surgical system can include functionality that is in addition to that supported by the master control system of the robotic surgical system, for example, the master control system 115 illustrated in FIG. 1. In some embodiments, the secondary controller(s) can be configured to communicate the status of the additional functions of the electromechanical components to the master control system 115. In other embodiments, the status of the additional functions of the electromechanical components can be communicated to an auxiliary control system, for example, auxiliary control system 1125 illustrated in FIG. 11. In one exemplary embodiment, additional functionality of an end effector, such as end effector 238, can be processed and controlled by a shaft secondary controller 1140 disposed within the shaft 236.

The shaft secondary controller 1140 can be configured to control additional functionality of an end effector 238. For example, the end effector 238 may have a second articulation joint that the master control system 115 of the robotic surgical system was not designed to control. A second pivot articulation solenoid can be disposed in the second articulation joint to facilitate determining, by the shaft secondary controller 1140, the angle of rotation of the second articulation joint.

At 1314, a process is illustrated for controlling and processing electromechanical components that require energy in addition to the energy provided by the robotic system. For example, the end effector 238 may have an electrode for cutting and cauterizing tissue. A puck secondary controller 1130 can be configured to control the waveform and magnitude of the current sent to the electrode at the end effector 238. The puck secondary controller 1140 can receive impedance and temperature data from one or more sensors disposed within the end effector 238, segmented electrode continuity data from the end effector 238, or the like. The impedance and temperature data can relate to the tissue of the patient. The puck secondary controller 1140 can be configured to control the waveform and magnitude of the current transmitted to the electrode of the end effector 238 based on information received from the electrode of the end effector 238. This waveform and magnitude control can occur without input from the master control system 115.

In some embodiments, the master control system 115 can be configured to facilitate activation of the electrode functionality of the end effector 238. In one embodiment, the master control system 115 can be configured to select the energy modality of the waveform. The energy modality can be selected based on clamp pressure of the end effector cutting tools. The puck secondary controller 1140 can be configured to transmit generator load and impedance information to the master control system 115, for display to a user of the robotic system. The generator load and impedance can be used to determine the clamp pressure by the master control system 115.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
    an electromechanical tool configured to perform surgical functions, the electromechanical tool including an instrument shaft and an end effector formed on the instrument shaft, wherein the end effector is configured to perform a procedure on tissue of a patient;
    an electromechanical arm configured for movement in multiple axes, wherein the electromechanical tool is configured to be mounted on the electromechanical arm, and the electromechanical tool is configured to move relative to the electromechanical arm;
    a master controller configured to control a set of basic functions of the electromechanical tool, the electromechanical arm, the instrument shaft, and the end effector, wherein one or more of the electromechanical tool, the electromechanical arm, the instrument shaft and the end effector are configured to perform a set of additional functions, wherein the master controller is configured to provide power to one or more of the electromechanical tool, the electromechanical arm, the instrument shaft and the end effector; and
    a secondary controller disposed on one or more of the electromechanical tool, the electromechanical arm, the instrument shaft, and the end effector, wherein the secondary controller is configured to:
    receive an activation signal from the master controller,
    determine one or more operating parameters associated with one or more of the electromechanical tool, the electromechanical arm, the instrument shaft and/or the end effector,
    control the set of additional functions of the electromechanical tool, the electromechanical arm, the instrument shaft and/or the end effector based on the determined one or more operating parameters following the reception of the activation signal.

2. The surgical system of claim 1, wherein the secondary controller controls the set of additional functions in response to receiving a request from the master controller.

3. The surgical system of claim 1, wherein the end effector further comprises
    a sensor configured to generate a sensor output and the secondary controller is in the end effector and is configured to control the set of additional functions of the end effector based on the generated output from the sensor.

4. The surgical system of claim 1, wherein the instrument shaft further comprises a status processor configured to monitor the status of the end effector.

5. The surgical system of claim 1, further comprising a puck, the puck comprising:
    a puck controller configured to:
    receive input from one or more sensors disposed on the instrument shaft and/or the end effector; and,
    control the movement of the instrument shaft and/or the end effector based on the input received from the one or more sensors disposed on the instrument shaft and/or end effector.

6. The surgical system of claim 5, wherein the puck controller is further configured to generate an output for transmission to the master controller, the output generated by the puck controller including a status of the puck, instrument shaft, and/or the end effector.

7. The surgical system of claim 5, wherein the puck controller is configured to control a rotation angle of the instrument shaft.

8. The surgical system of claim 5, wherein the puck controller is configured to control a rotation of the distal head of the end effector.

9. The surgical system of claim 1, wherein the instrument shaft comprises:
    a first articulation joint controlled by an input received from the master controller;
    a second articulation joint; and
    an instrument shaft controller configured to control the movement of the second articulation joint.

10. The surgical system of claim 9, wherein the instrument shaft controller is configured to transmit a status of the second articulation joint to the master controller.

11. The surgical system of claim 9, further comprising a puck configured to control one or more of the functions of the instrument shaft and/or the end effector and wherein the instrument shaft controller is configured to transmit a status of the second end articulation joint to the puck.

12. The surgical system of claim 11, wherein the end effector includes an ultrasound transducer.

13. The surgical system of claim 1, further comprising a user interface, the user interface comprising a user control having a plurality of modes, wherein one mode of the plurality modes is configured to facilitate activation of the set of additional functions of the electromechanical tool, the electromechanical arm, the instrument shaft and/or the end effector.

14. A method of controlling electromechanical tools of a robotic surgical system, the method comprising:
    generating a signal at a master controller to control one or more basic surgical functions of one or more electromechanical tools of a robotic surgical system, the one or more electromechanical tools disposed downstream of the master controller and configured to perform one or more basic surgical functions and one or more additional surgical functions;

determining, by a secondary controller operatively associated with the one or more electromechanical tools of the robotic surgical system, one or more operating parameters associated with the one or more electromechanical tools;

receiving, by the secondary controller, an activation signal from the master controller;

generating a control signal, by the secondary controller based on the determined one or more operating parameters, to control the one or more additional functions of the one or more electromechanical tools following the reception of the activation signal;

generating a sensor output from a sensor disposed at the end effector, the end effector having basic surgical functions and additional surgical functions; and controlling, by a secondary controller disposed in the end effector, the additional functions of the end effector.

15. A method of claim 14, wherein the one or more electromechanical tools includes an instrument shaft and an end effector formed on the instrument shaft, wherein the end effector is configured to perform a procedure on tissue of a patient.

16. The method of claim 14, wherein the one or more secondary controllers are configured to control the one or more additional functions in response to receiving a request from the master controller.

17. The method of claim 14, further comprising monitoring the status of the end effector.

18. The method of claim 14, further comprising:

receiving, at a secondary controller disposed within a puck of the robotic surgical system, input from one or more sensors disposed on the instrument shaft and/or the end effector; and controlling, by the secondary controller disposed within the puck, the movement of the instrument shaft and/or the end effector based on the input received from the one or more sensors disposed on the instrument shaft and/or end effector.

19. The method of claim 18, further comprising:

generating, at one or more of the secondary controllers, an output for transmission to the master controller, the output including a state of the one or more electromechanical components.

20. The surgical system of claim 6, wherein the puck controller is further configured to control a rotation angle of the instrument shaft.

* * * * *